United States Patent [19]
Kensey

[11] Patent Number: 6,022,333
[45] Date of Patent: Feb. 8, 2000

[54] METHOD AND SYSTEM FOR REMOVING MATERIALS FROM LYMPHATIC AND OTHER FLUIDS

[75] Inventor: Kenneth Kensey, Chester Springs, Pa.

[73] Assignee: S.L.I.M. Tech, Ltd., Exton, Pa.

[21] Appl. No.: 08/847,262

[22] Filed: May 1, 1997

[51] Int. Cl.⁷ .................................................. A61M 37/00
[52] U.S. Cl. ................................................. 604/5; 604/29
[58] Field of Search ............................. 604/4–6, 28–30, 604/32, 8–10

[56] References Cited

U.S. PATENT DOCUMENTS

| | | |
|---|---|---|
| 3,929,130 | 12/1975 | Hargest . |
| 4,235,231 | 11/1980 | Schindler et al. .................. 128/214 |
| 4,261,341 | 4/1981 | Hakim et al. ........................ 128/1 |
| 4,610,658 | 9/1986 | Buchwald et al. .................. 604/9 |
| 4,612,007 | 9/1986 | Edelson . |
| 4,741,739 | 5/1988 | Dormandy, Jr. ..................... 604/8 |
| 4,769,037 | 9/1988 | Midcalf ............................... 623/12 |
| 5,092,886 | 3/1992 | Dobos-Hardy . |
| 5,104,729 | 4/1992 | Stedronsky ......................... 428/304 |
| 5,141,493 | 8/1992 | Jacobsen etal. .................... 604/29 |
| 5,152,743 | 10/1992 | Gorsuch et al. .................... 604/4 |
| 5,391,143 | 2/1995 | Kensey . |
| 5,474,526 | 12/1995 | Danielson et al. ................. 604/4 |
| 5,490,937 | 2/1996 | Van Reis . |
| 5,545,131 | 8/1996 | Davankov . |

*Primary Examiner*—Corrine McDermott
*Assistant Examiner*—David J. Cho
*Attorney, Agent, or Firm*—Caesar, Rivise, Bernstein, Cohen & Pokotilow, Ltd.

[57] ABSTRACT

Method and systems for separating a first material, e.g., cholesterol or fat, from lymphatic fluid flowing through a duct within the body of a living being, so that the material is removed from the being's body or recirculated. The system includes a filter for separating that material, and an elongated conduit implanted within the vascular system and having a distal end in fluid communication with the duct and a proximal end in fluid communication with the filter. An implantable pump may be provided to enhance the operation of the system.

21 Claims, 6 Drawing Sheets

METHOD AND SYSTEM FOR REMOVING MATERIALS FROM LYMPHATIC AND OTHER FLUIDS

BACKGROUND OF THE INVENTION

This invention relates generally to medical devices and methods of removing one or more materials from the lymphatic fluid in a living being's body, and more particularly to systems and methods for effecting cholesterol and weight reduction of living beings by removing cholesterol and fat from the lymphatic fluid thereof.

High levels of cholesterol are linked with atherosclerosis. In many individuals, cholesterol can be maintained at desirable levels through diet and/or medication. However, some individuals cannot adhere to dietary rules and some individuals do not respond well to drug therapy.

Obesity control is of considerable concern to the medical community, as well as to the public at large, for medical as well as cosmetic reasons. While sensible eating and exercise are deemed to be the best methods for effecting weight loss and maintaining a desired weight, for many persons such techniques are unsuccessful or unavailing.

Although my prior U.S. Pat. No. 5,391,143 provides means for addressing similar needs, there is still room for alternative systems and methods for controlling cholesterol and obesity.

OBJECTS OF THE INVENTION

Accordingly, it is a general object of this invention to provide systems and methods of use which address the foregoing needs.

It is another object of this invention to provide systems and methods of use for effecting the removal of one or more predetermined materials found in the lymphatic fluid by draining a portion of that fluid from the being's body.

It is a further object of this invention to provide systems and methods of use for effecting the removal of cholesterol and fat from the body of a being by drainage of a portion of lymphatic fluid from the being's body.

It is a further object of this invention to provide implantable systems and methods of use for effecting the removal of cholesterol, fat or other lymphatic carried components from the body of a being by filtration and drainage of a portion of lymphatic fluid from the being's body.

SUMMARY OF THE INVENTION

These and other objects of this invention are achieved by providing methods and systems for removing at least one predetermined material, e.g., cholesterol or fat, from the body of a living being by gaining access to a duct through which lymphatic fluid containing the material flows, and withdrawing the lymphatic fluid and the material from the duct.

The system is implantable within the being s body and basically comprises a filter and first, second and third conduit means. The first conduit means, e.g., an elongated flexible catheter, is configured to be located within the body of the being, e.g., is suitable for location within the vascular system, and coupled to a duct having lymphatic fluid flowing therethrough so that said lymphatic fluid flows into the conduit means. The first conduit means, e.g., a proximal portion thereof, is coupled to the filter for carrying the lymphatic fluid to said filter. The filter is operable, e.g., utilizes gravity and/or the hydraulic pressures generated by the being, to cause the material to be removed, e.g., the cholesterol and/or fat, in the lymphatic fluid to be separated therefrom, whereupon that material can be removed from the body of the being.

The second conduit is coupled to the filter and to a first internal portion of the body of the being, e.g., the peritoneum, a portion of the gastrointestinal tract, the venous system, or the lung, for carrying the lymphatic fluid remaining after the separation of the material to be removed therefrom to that first internal portion for reabsorption thereby. Such action can be carried out continuously or repeatedly at regular or irregular intervals. The third conduit is coupled to the filter and to a second internal portion of the body of the being, e.g., the urinary bladder, for carrying the material to be removed, after it has been separated from the lymphatic fluid, to the second internal portion for excretion thereby.

In accordance with the method of this invention, the first conduit is coupled to a duct within the body of the being having lymphatic fluid flowing therethrough so that fluid flows into and through the first conduit, whereupon the at least one material to be removed within the lymphatic fluid is removed from the body of the being continually, i.e., continuously or repeatedly at regular or irregular intervals, over an extended period of time.

All references cited herein are incorporated by reference herein in their entireties.

BRIEF DESCRIPTION OF THE DRAWINGS

Other objects and many of the attendant advantages of this invention will be readily appreciated as the same becomes better understood by reference to the following detailed description when considered in connection with the accompanying drawings wherein.

DETAILED DESCRIPTION OF PREFERRED EMBODIMENTS

Figure 1:
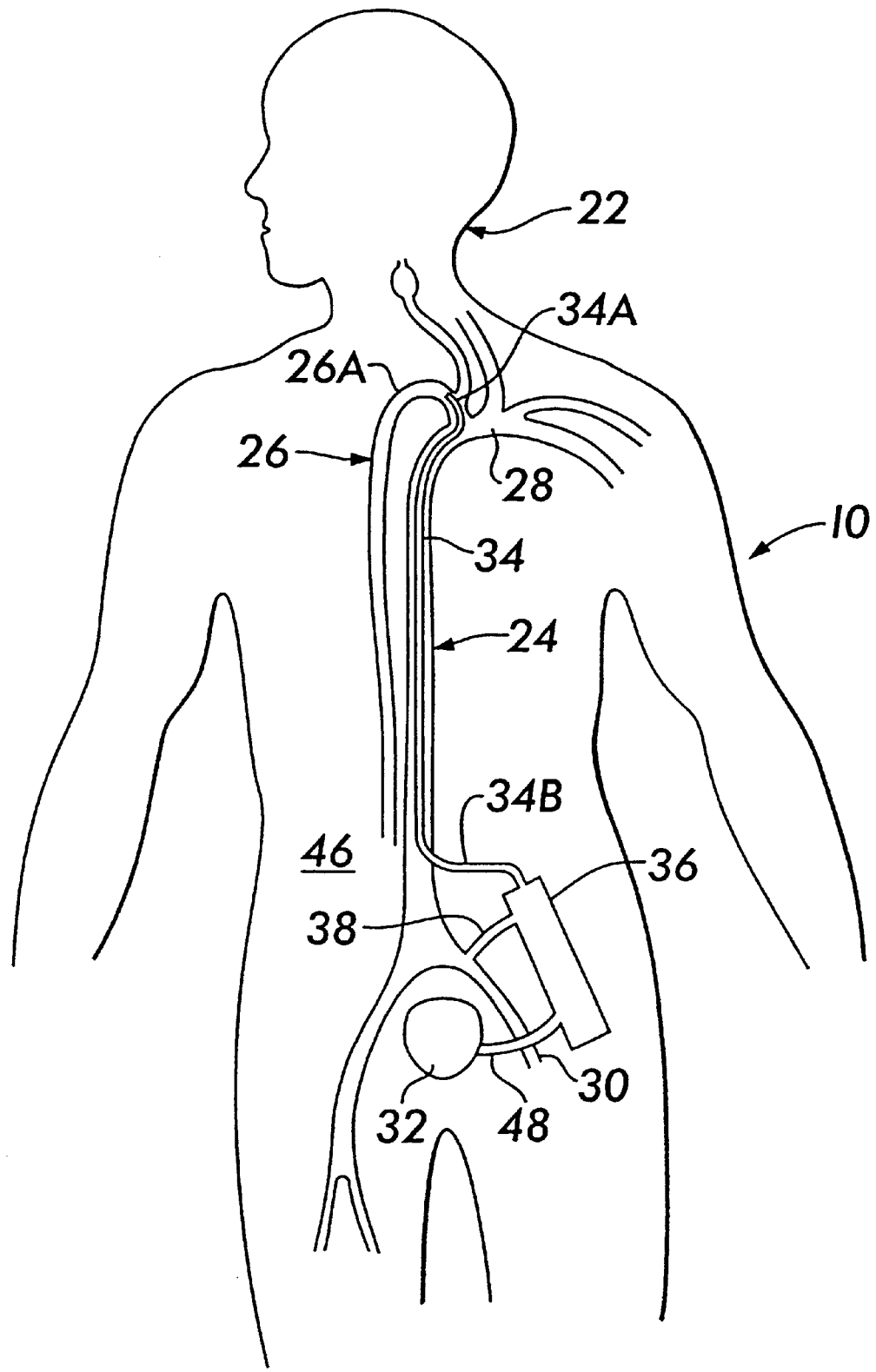
FIG. 1 is a schematic diagram of a portion of the body of a living person showing one embodiment of the system of this invention connected thereto.

Referring now in greater detail to the figures, there is shown at 10, 100, 200, 300, and 400 in FIGS. 1–5, respectively, systems constructed in accordance with the teachings of this invention for removing one or more predetermined materials from lymphatic fluid flowing through the body of a living being 22. In accordance with one preferred aspect of this invention, and which will be described in detail hereinafter, the material removed by those systems comprises fat and/or cholesterol. Accordingly, the systems of this invention are particularly suitable for use as a viable means for cholesterol reduction, weight reduction, obesity control and reducing blood viscosity. It should, however, be pointed out that this is just one application of the subject invention. Thus, the systems and methods of this invention can be used to effect the removal of one or more other materials, such as phosphoglycerides and triglycerides, from the lymphatic fluid or other bodily fluids for various reasons. Notwithstanding those various applications of this invention, the remainder of this detailed description will address the construction and usages of the various inventive systems for cholesterol reduction, weight reduction and obesity control.

Before describing such systems, a brief description of the portion of the body of the being 22 shown in the various figures is in order. As is known, the thoracic duct usually merges into its associated subclavian vein. Each of the figures of this drawing shows a portion of the being's venous system 24 and the lymphatic system 26 to which the various inventive systems 10–400 are coupled. As should be appreciated by those skilled in the art, the anatomic structures shown herein are greatly simplified views, e.g., only the thoracic duct and its associated subclavian vein are shown. The thoracic duct is designated by the reference numeral 26A and its associated subclavian vein by the reference numeral 28. The femoral vein and the urinary bladder are also shown in the various figures and are designated by the reference numerals 30 and 32, respectively. Other anatomical structures which are shown in various specific figures will be identified and discussed later.

The first embodiment of a system constructed in accordance with this invention to be discussed is the system 10 of FIG. 1. That system basically comprises a drainage lumen 34, a filter assembly 36, and a pair of outlet conduits 38 and 48. Each system of this invention makes use of a drainage lumen. That lumen can be of any suitable construction for implantation and long-term residence within the body of the being 22, e.g., extending through the venous system or subcutaneously or through some other suitable internal passageway. In the embodiment 10 shown in FIG. 1., the drainage lumen 34 is an elongated conduit formed of a flexible biocompatible material, e.g., a medical grade plastic like that used in vascular catheters, having a distal end 34A and a proximal end 34B. It is particularly preferred to use a lumen made of or coated with phosphoryl choline. Phosphoryl choline compounds are available from Biocompatibles, Ltd., Uxbridge, UK. The lumen 34 is located within and extends through a portion of the venous system 24 so that its distal end 34A is in fluid communication with the interior of the thoracic duct 28 and its proximal end 34B exits from the venous system in the region of the being's abdomen 46. The proximal end of the lumen 34 is in fluid communication with the filter assembly 36. Accordingly, at least a portion of the lymphatic fluid flowing through the thoracic duct drains into the lumen 34 and is carried through the lumen to the filter assembly 36.

The filter assembly 36 is an implantable device, which is implanted in the being at any suitable location, e.g., in the abdominal area. The filter assembly 36 includes a filter (e.g., a filtration membrane), and a pair of outlet ports in fluid communication with the outlet conduits 48 and 38, respectively, to carry the filtrate containing the material to be removed and the remaining lymphatic fluid (i.e., the retentate), respectively, out of the filter assembly 36. In particular, the outlet port which is in communication with the conduit 38 is in fluid communication with the interior portion of the filter assembly through which the lymphatic fluid minus the separated material passes. That conduit is also coupled to and in fluid communication with the femoral vein 30. Accordingly, the lymphatic fluid minus the separated material flows from the filter assembly 36 on to the venous system 24 continuously for reabsorption by the being. It is necessary to recycle the lymphatic fluid containing the lymphatic cells to preserve the health of the being.

The outlet port which is in communication with the conduit 48 is also in fluid communication with the interior portion of the filter assembly 36. The conduit 48 is in fluid communication with the excretory system of the individual, in this case the urinary bladder 32.

Figure 2:
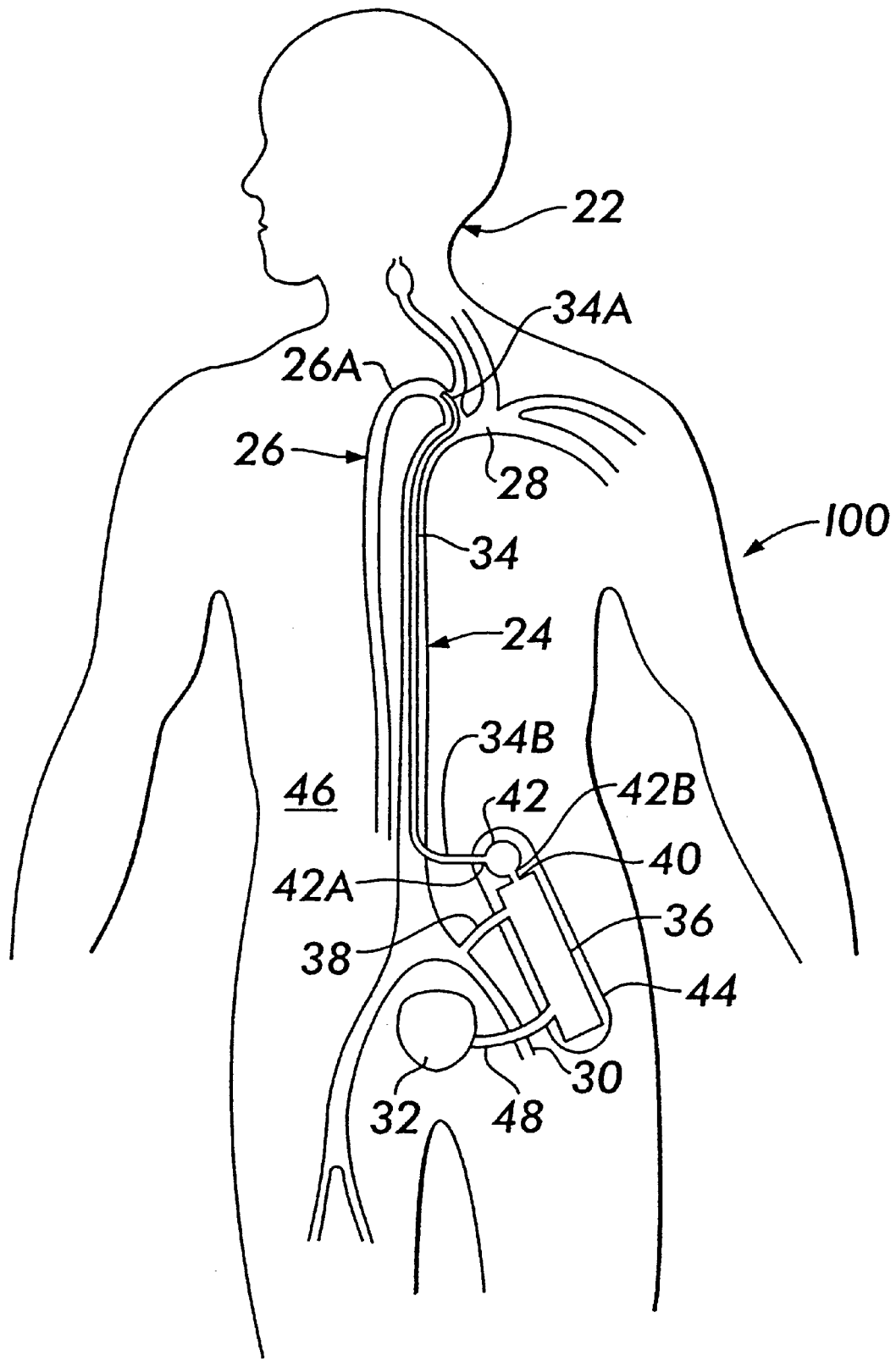
FIG. 2 is a schematic diagram like that of FIG. 1 but showing an alternative embodiment of the system of this invention.

In the embodiment depicted in FIG. 2, the proximal end 34B is coupled to and in fluid communication with a pump 42. The pump is also an implantable device, which can be of any suitable construction for pumping the fluid into the filter 36 and pumping the filtrate and retentate out of the filter assembly 36, optionally under control from outside the body of the being. Preferably, the pump is a peristaltic pump. The pump 42 can be placed upstream and/or downstream with respect to the filter assembly 36. FIG. 2 depicts an embodiment in which the pump 42 is placed upstream of the filter assembly 36 within a housing 44 and includes an inlet port 42A in fluid communication with the proximal end of the lumen 34 and an outlet port 42B in fluid communication with a conduit 40. The opposite end of the conduit 40 is in fluid communication with the filter assembly 36.

Suitable pumps may be operated manually (such as by externally applied pressure) or in response to changes in lymphatic fluid parameters, or by external control accomplished electrically, electrostatically, or magnetically by means located outside the being's body so that no access port is necessary through the being's body to effect pump control. Moreover, the pump 42 may be operated under computer control to effect operation at desired times or in response to monitored parameters or patient conditions.

The systems 10, 100, 300 and 400 shown in FIGS. 1 and 3–5 make use of the being's urinary bladder 32 to excrete or remove the filtrate, including the matter to be removed from his/her body. Accordingly, as can be seen, the outlet conduit 48 from the filter assembly 36 is coupled to and in fluid communication with the being's urinary bladder 32. With such an arrangement, the removed materials can be pumped to the urinary bladder when desired, e.g., continuously, periodically, or irregularly, so that the materials will be excreted from the body with urine.

Figure 3:
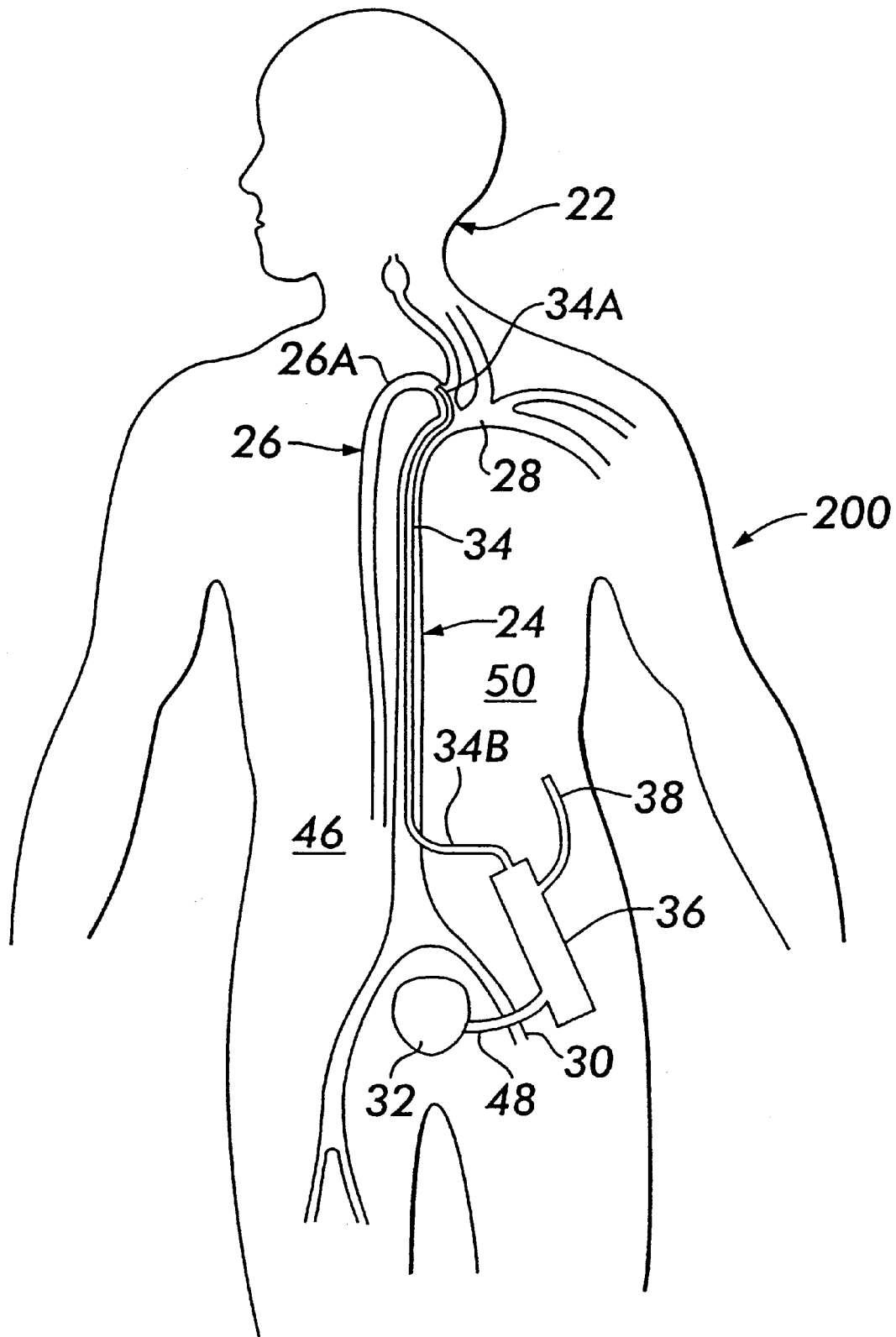
FIG. 3 is a schematic diagram like that of FIG. 1 but showing another alternative embodiment of the system of this invention.

The system 200 shown in FIG. 3 also makes use of the being's urinary bladder 32 to excrete or remove the separated materials from his/her body, and in this respect is identical in construction to the system 100. However, unlike the system 100, it makes use of the peritoneum 50 for effecting the reabsorption of the lymphatic fluid, whereas system 100 makes use of the venous system 24, e.g., the femoral vein. Since the components of the system 200 are the same as those of the system 100 they are given the same reference numerals and the details of their construction and operation will not be reiterated.

As can be seen in FIG. 3, the outlet conduit 38 from the filter assembly 36 is coupled to, and in fluid communication with, the being's peritoneum 50 so that lymphatic fluid minus the separated materials is provided to the peritoneum for reabsorption.

Figure 4:
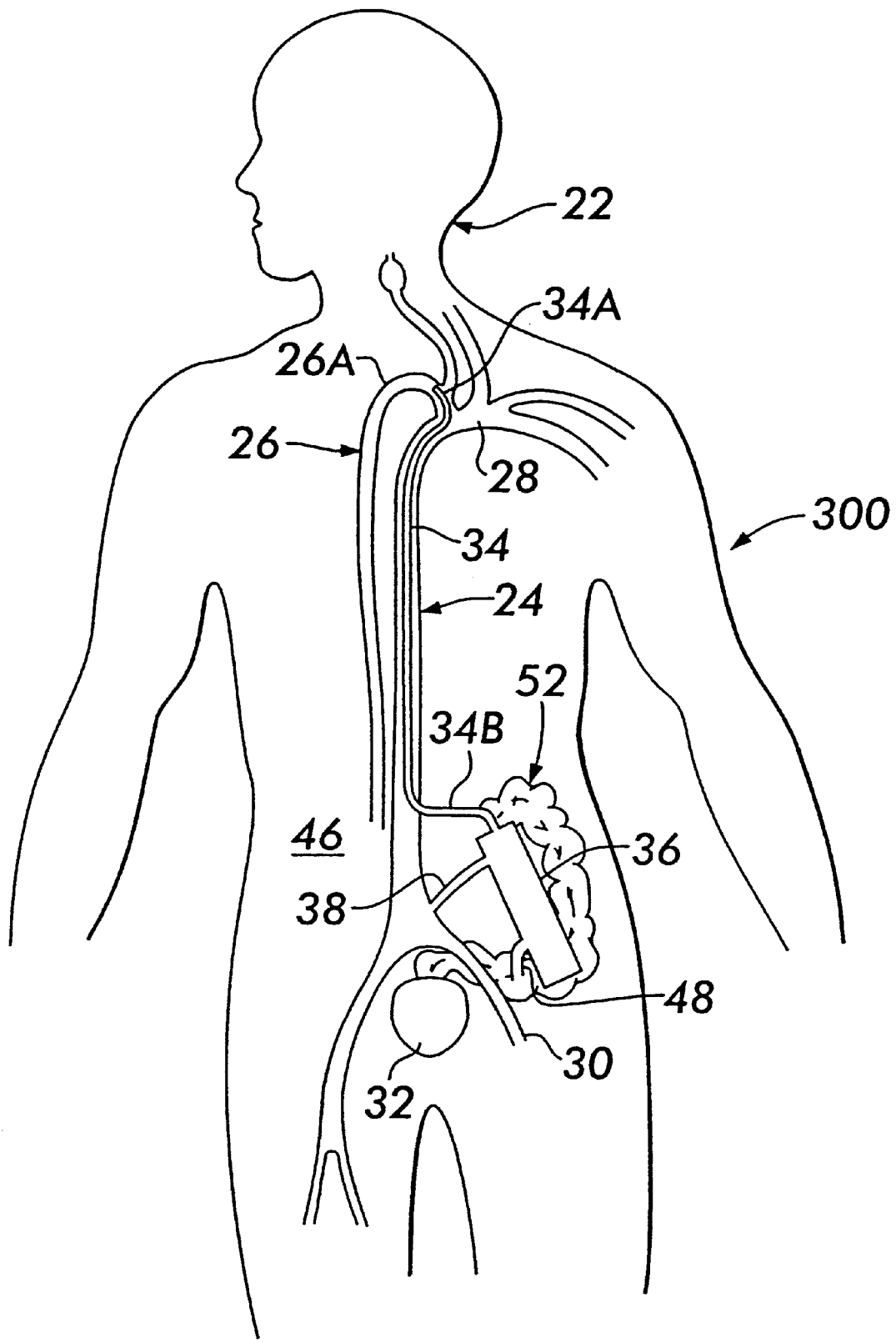
FIG. 4 is a schematic diagram like that of FIG. 1 but showing yet another alternative embodiment of the system of this invention.

The system 300 shown in FIG. 4 is like the embodiment 100 of FIG. 2 in that it makes use of the venous system 24 for reabsorption of the lymphatic fluid minus the removed fat. However, unlike system 100, the system 300 makes use of the being's gastrointestinal tract, e.g., the bowel 52, to excrete or remove the separated material from his/her body. The system 300 is identical in construction to the system 100 so that the same components of those systems are given the same reference numerals and the details of their construction and operation will not be reiterated.

As can be seen in FIG. 4, the outlet conduit 48 from the filter assembly 36 is coupled to, and in fluid communication with the being's bowel 52. With such an arrangement the removed material can be pumped to the gastrointestinal tract, e.g., the bowel, when desired, e.g., continuously, periodically, or irregularly, so that the material will be excreted from the body with feces. It should be noted that if the material withdrawn from the lymphatic system by this invention, e.g., the fat, is introduced into a suitable upper portion of the gastrointestinal tract, it may be at least partially reabsorbed therein, thereby reducing the person's hunger.

Figure 5:
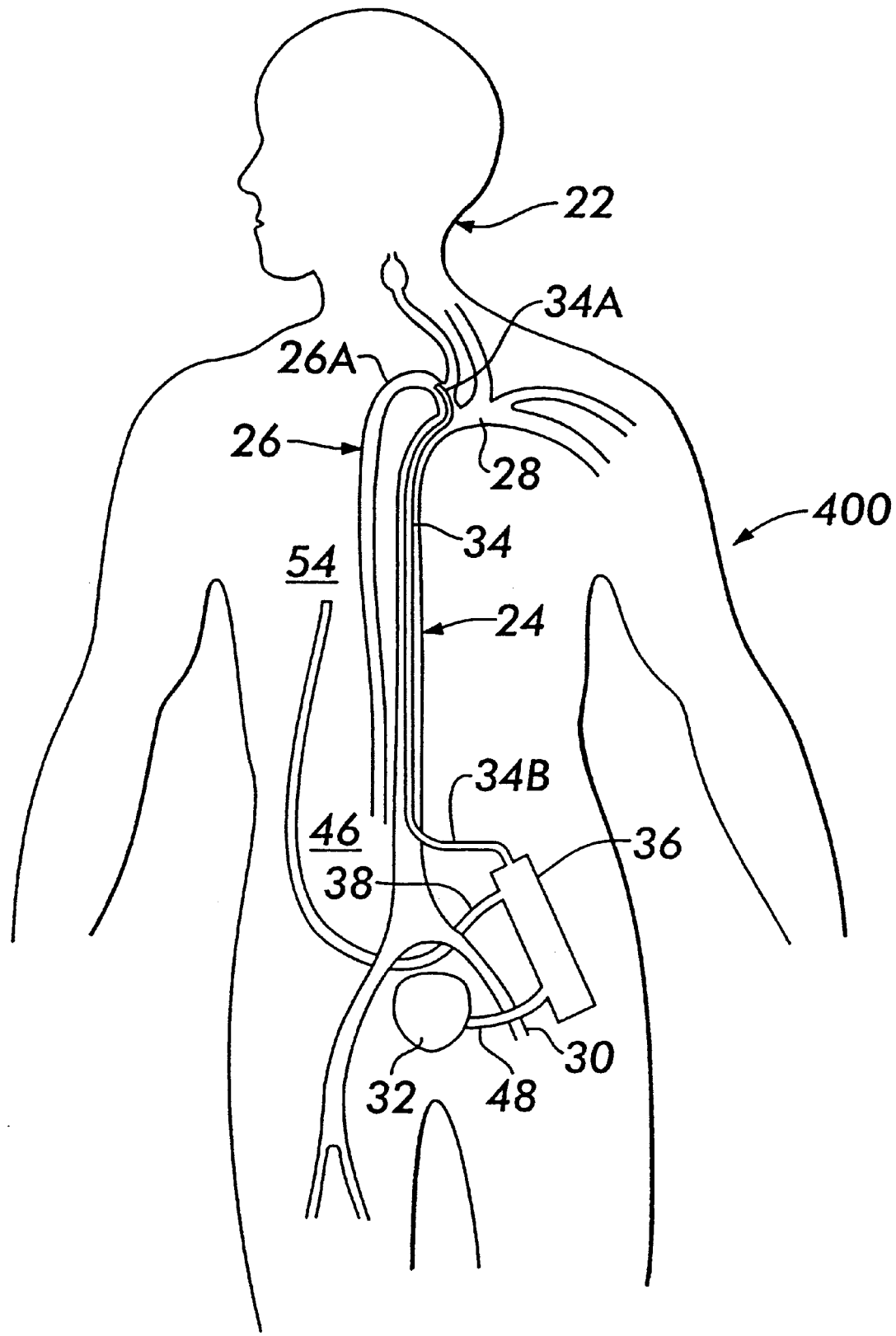
FIG. 5 is a schematic diagram like that of FIG. 1 but showing still another alternative embodiment of the system of this invention.

The system 400 shown in FIG. 5 is largely identical in construction to the system 200 in FIG. 3 and also makes use of the being's urinary bladder 32 to excrete or remove the separated fat from his/her body. However, the system 400 makes use of the thoracic cavity 54 for effecting the reabsorption of the lymphatic fluid, whereas system 300 makes use of the peritoneum 50. As before, since the components of the system 400 are the same as those of system 200, they are given the same reference numerals and the details of their construction and operation will not be reiterated. As can be seen in FIG. 5, the outlet conduit 38 from the filter assembly 36 is coupled to, and in fluid communication with, the being's thoracic cavity 54 so that lymphatic fluid minus the separated matter is provided to that cavity for reabsorption.

In all of the systems described heretofore, the drainage lumen or conduit 34 is located within and extends through the venous system. As mentioned earlier and as should be reiterated herein, that arrangement is not the only arrangement contemplated by this invention. Thus, for example, the drainage lumen 34 can be implanted subcutaneously between the thoracic duct and the abdomen, or any other place at which the filter assembly and optionally associated pump are implanted.

Figure 6:
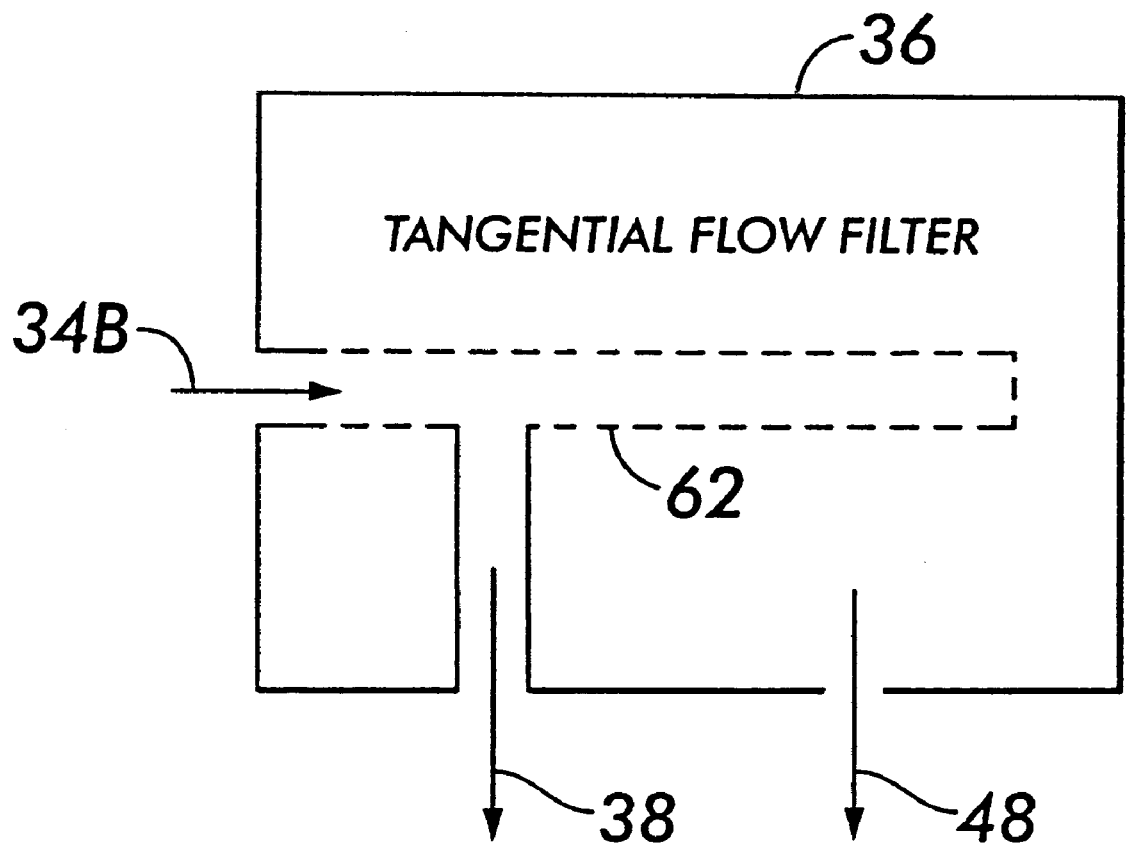
FIG. 6 is a schematic diagram showing a filter assembly according to the invention in greater detail.

FIG. 6 depicts an embodiment of the filter assembly 36 according to the invention. The filter assembly 36 is preferably a tangential flow filter assembly made of, or coated with, a biocompatible material, such as phosphoryl choline. Tangential flow filters are available from, for example, Spectrum Medical Industries, Inc., Houston, Tex. The pore size of the filter assembly's porous filtration membrane 62 is selected to permit material to be removed (e.g., cholesterol and fat) to pass through the porous membrane 62 and out of the outlet conduit 48, while larger molecules continue along the flow path as retentate and exit the filter assembly 36 through outlet conduit 38.

The pore size of the porous membrane 62 can be selected based on the size of the material to be filtered out of the fluid.

It should also be pointed out at this juncture that the systems and methods of this invention need not make use of all of the components described heretofore.

Without further elaboration the foregoing will so fully illustrate my invention that others may, by applying current or future knowledge, adopt the same for use under various conditions of service.

I claim:

1. A method for removing at least one material from a body of a living being, said method comprising:

shunting lymphatic fluid containing said at least one material from a lymphatic duct through an artificial filter assembly to provide (i) a filtrate which passes through a filtration membrane of said filter assembly, wherein said filtrate contains said at least one material, and (ii) a retentate which does not pass through said filtration membrane, wherein said filtration membrane has pores sufficiently large to allow said at least one material to pass through the porous membrane, and sufficiently small to prevent at least the body's lymphatic cells from passing through the porous membrane;

expelling said retentate from said filter assembly such that said retentate is reabsorbed by said body's lymphatic system and;

expelling said filtrate from said filter assembly to a portion of said body's excretory system for excretion by said body, thereby removing said at least one material from said body.

2. The method according to claim 1, wherein said lymphatic duct is a thoracic duct.

3. The method according to claim 1, wherein said retentate is expelled from said filter assembly into said body's femoral vein for said reabsorption into said lymphatic system.

4. The method according to claim 1, wherein said retentate is expelled from said filter assembly into said body's peritoneum for said reabsorption into said lymphatic system.

5. The method according to claim 1, wherein said retentate is expelled from said filter assembly into said body's thoracic cavity for said reabsorption into said lymphatic system.

6. The method according to claim 1, wherein said filtrate is expelled from said filter assembly into said body's urinary bladder for excretion from said body.

7. The method according to claim 1, wherein said filtrate is expelled from said filter assembly into said body's bowel for excretion from said body.

8. The method according to claim 1, wherein said lymphatic fluid is shunted from said lymphatic duct to said filter assembly through a lumen comprising phosphoryl choline.

9. The method according to claim 1, wherein said retentate is expelled from said filter assembly through an outlet conduit leading from said filter assembly to a portion of said body selected from the group consisting of a vein, a peritoneum and a thoracic cavity, and wherein said outlet conduit comprises phosphoryl choline.

10. The method according to claim 1, wherein said filtrate is expelled from said filter assembly through an outlet conduit leading from said filter assembly to said excretory system portion of said body, and wherein said outlet conduit comprises phosphoryl choline.

11. The method according to claim 1, wherein said filtrate is substantially free of lymphatic cells.

12. The method according to claim 11, wherein at least about 50% of said lymphatic cells entering said filter assembly exit said filter assembly in said retentate.

13. The method according to claim 11, wherein at least about 75% of said lymphatic cells entering said filter assembly exit said filter assembly in said retentate.

14. The method according to claim 11, wherein at least about 90% of said lymphatic cells entering said filter assembly exit said filter assembly in said retentate.

15. The method according to claim 1, wherein said method is for effecting obesity control of said being and wherein said at least one material comprises fat.

16. The method according to claim 1, wherein said method is for controlling a cholesterol concentration in said being and wherein said at least one material comprises cholesterol.

17. The method according to claim 1, wherein said method is conducted without artificial pumping means.

18. The method according to claim 1, wherein said method is conducted with artificial pumping means to facilitate passage of said lymphatic fluid through said filter assembly.

19. The method according to claim 1, wherein said lymphatic fluid is shunted from said lymphatic duct to said filter assembly through a lumen implanted intravenously.

20. The method according to claim 1, wherein said lymphatic fluid is shunted from said lymphatic duct to said filter assembly through a lumen implanted subcutaneously.

21. The method according to claim 1, wherein said filter assembly filters said lymphatic fluid tangentially.

* * * * *